United States Patent
Lee et al.

(10) Patent No.: US 9,737,119 B2
(45) Date of Patent: Aug. 22, 2017

(54) WATCH TYPE TERMINAL

(71) Applicant: LG ELECTRONICS INC., Seoul (KR)

(72) Inventors: Yongho Lee, Seoul (KR); Kwanghyun Ahn, Seoul (KR); Junho Yang, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 16 days.

(21) Appl. No.: 15/006,895

(22) Filed: Jan. 26, 2016

(65) Prior Publication Data

US 2017/0000222 A1    Jan. 5, 2017

(30) Foreign Application Priority Data

Jul. 3, 2015    (KR) .................. 10-2015-0095394

(51) Int. Cl.

| | |
|---|---|
| G06F 13/40 | (2006.01) |
| A44C 5/14 | (2006.01) |
| A44B 11/20 | (2006.01) |
| A61B 5/00 | (2006.01) |
| G04G 17/08 | (2006.01) |
| G06F 1/16 | (2006.01) |
| H04B 1/3827 | (2015.01) |
| H04M 1/02 | (2006.01) |
| H04M 1/725 | (2006.01) |
| A44C 5/20 | (2006.01) |

(Continued)

(52) U.S. Cl.
CPC .............. *A44C 5/147* (2013.01); *A44B 11/20* (2013.01); *A44C 5/14* (2013.01); *A44C 5/2071* (2013.01); *A61B 5/681* (2013.01); *G04G 17/06* (2013.01); *G04G 17/083* (2013.01); *G06F 1/163* (2013.01); *G06F 1/1683* (2013.01); *H04B 1/385* (2013.01); *H04M 1/0254* (2013.01); *H04M 1/72527* (2013.01); *A44C 5/0007* (2013.01); *A44C 5/10* (2013.01); *H04B 2001/3861* (2013.01)

(58) Field of Classification Search
CPC ........................................................ G06F 3/01
USPC .................................................... 361/679.21
See application file for complete search history.

(56) References Cited

U.S. PATENT DOCUMENTS

| | | | |
|---|---|---|---|
| 2001/0043514 A1 | 11/2001 | Kita | |
| 2007/0180857 A1* | 8/2007 | Giordano | ............... A44C 5/22 63/3.2 |
| 2013/0271350 A1 | 10/2013 | Lyons | |

FOREIGN PATENT DOCUMENTS

| | | |
|---|---|---|
| JP | S49108083 | 10/1974 |
| WO | 2005083546 | 9/2005 |

(Continued)

OTHER PUBLICATIONS

European Patent Application No. 16174788.6, Search Report dated Jan. 11, 2017, 14 pages.

(Continued)

*Primary Examiner* — Jerry Wu
(74) *Attorney, Agent, or Firm* — Lee, Hong, Degerman, Kang & Waimey

(57) ABSTRACT

A watch type terminal includes a main body, and a strap connected to the main body. In the watch type terminal, the strap includes one or more modules each having a specific function, and one or more partition straps having the one or more modules respectively received thereat. In the strap, the module and the partition strap are electrically connected to each other.

18 Claims, 16 Drawing Sheets

(51) Int. Cl.
*G04G 17/06* (2006.01)
*A44C 5/00* (2006.01)
*A44C 5/10* (2006.01)

(56) References Cited

FOREIGN PATENT DOCUMENTS

| WO | 2014012486 | 1/2014 |
| WO | 2015100224 | 7/2015 |
| WO | 2016048654 | 3/2016 |

OTHER PUBLICATIONS

European Patent Application No. 16174788.6, Partial Search Report dated Dec. 1, 2016, 9 pages.

* cited by examiner

WATCH TYPE TERMINAL

CROSS-REFERENCE TO RELATED APPLICATIONS

Pursuant to 35 U.S.C. §119(a), this application claims the benefit of earlier filing date and right of priority to Korean Patent Application No. 10-2015-0095394, filed on Jul. 3, 2015 the contents of which are hereby incorporated by reference herein in its entirety.

BACKGROUND OF THE DISCLOSURE

1. Field of the Disclosure

The present disclosure relates to a watch type terminal capable of implementing various functions by using a strap.

2. Description of the Conventional Art

Terminals may be generally classified as mobile/portable terminals or stationary terminals according to their mobility. Mobile terminals may also be classified as handheld terminals or vehicle mounted terminals according to whether or not a user can directly carry the terminal.

Mobile terminals have become increasingly more functional. Examples of such functions include data and voice communications, capturing images and video via a camera, recording audio, playing music files via a speaker system, and displaying images and video on a display. Some mobile terminals include additional functionality which supports game playing, while other terminals are configured as multimedia players. More recently, mobile terminals have been configured to receive broadcast and multicast signals which permit viewing of content such as videos and television programs.

Efforts are ongoing to support and increase the functionality of mobile terminals. Such efforts include software and hardware improvements, as well as changes and improvements in the structural components.

In the case of a watch type terminal, many components cannot be mounted in the watch type terminal having a narrow component mounting space as compared with other electronic devices, and therefore, it is impossible to implement various functions. If many components are intended to be mounted in the watch type terminal, the size of the watch type terminal increases. Thus, it is required to develop a watch type terminal in consideration of user's convenience.

SUMMARY OF THE DISCLOSURE

Therefore, an aspect of the detailed description is to provide a watch type terminal capable of implementing various functions according to user's convenience.

To achieve these and other advantages and in accordance with the purpose of this specification, as embodied and broadly described herein, a watch type terminal includes: a main body; and a strap connected to the main body, wherein the strap includes: one or more modules each having a specific functions; and one or more partition straps having the one or more modules respectively received thereat, wherein the module and the partition strap are electrically connected to each other.

In one exemplary embodiment, the watch type terminal may include an attaching/detaching pin formed at least one side of the partition strap the attaching/detaching pin being formed toward the inside the partition strap by penetrating the partition strap; and an elastic member provided at a position opposite to the attaching/detaching pin to attach/detach the module to/from the partition strap by providing an elastic force to the attaching/detaching pin.

In one exemplary embodiment, a first hook may be formed at an end portion of the attaching/detaching pin, and a second hook latched to the first hook may be formed at a bottom surface of the module.

In one exemplary embodiment, the strap may further include a first strap connected to the main body, the first strap being provided with a first flexible circuit board electrically connected to a main circuit board provided to the main body; and a second strap separably fastened to the first strap, the second strap being provided with a second flexible circuit board electrically connected to the first flexible circuit board. The partition strap may be provided with a third flexible circuit board electrically connected to the second strap to be electrically connected to the second flexible circuit board, and the one or more partition straps and the second strap may be connected to each other by a pair of internal frames respectively formed at both sides thereof.

In one exemplary embodiment, the third flexible circuit board may include a supporting portion provided at the inside of the internal frame, the supporting portion having a plurality of through-holes formed therein; and a connecting portion extending from the supporting portion, the connecting portion being connected to the second flexible circuit board.

In one exemplary embodiment, the internal frame may include a fixing frame fixed to each partition strap; and a connecting frame connected to the fixing frame, the connecting frame connecting two or more partition straps formed adjacent to each other or connecting the partition strap and the second strap to each other.

In one exemplary embodiment, both ends of the fixing frame and the connecting frame may be fixed by a hinge such that the fixing frame and the connecting frame are connected to be individually rotatable. The hinge may be inserted into the through-hole formed in the supporting portion to fix the internal frame to the third flexible circuit board.

In one exemplary embodiment, the partition strap may include a wall portion to which the internal frames and the third flexible circuit board are provided; and a bottom portion formed vertically from the wall portion, the bottom portion having a through-hole formed therein to support the module.

In one exemplary embodiment, the third flexible circuit board may be provided with a first contact terminal extending from a lower portion of the supporting portion to be received at the bottom portion, and a second contact terminal disposed at a lower end of the module to be contacted with the first contact terminal, so that the module and the partition strap are electrically connected to each other.

In one exemplary embodiment, the first and second contact terminals may be waterproof-coated.

In one exemplary embodiment, the module may include an internal circuit board electrically connected to the third flexible circuit board; and a battery for operating the module.

In one exemplary embodiment, a charging terminal for charging the battery may be provided at a lower surface of the module.

In one exemplary embodiment, the charging terminal may be formed to be exposed to one surface of the module, and an O-ring surrounding the charging terminal may be provided around the charging terminal.

In one exemplary embodiment, the strap may be separated at least one portion, and may further include, at the separated portion, a first connecting strap provided further outward and a second connecting strap provided at the inside of the first connecting strap, the second connecting strap having at least one portion disposed to overlap the first connecting strap. The size of the overlapping portion of the first and second connecting straps may be adjusted, so that the length of the strap is changed.

In one exemplary embodiment, the watch type terminal may further include a connecting member having throughholes formed along a first direction of the first and second connecting straps such that at least portions of the first and second connecting straps are inserted into the connecting member; a button portion having a guide groove formed along the first direction in the first connecting strap, and the button portion moving on the guide groove; and an elastic member provided at a lower portion of the button portion to provide an elastic force to the button portion.

In one exemplary embodiment, the second connecting strap may be fixed by a fixing guide formed inside the connecting member.

In one exemplary embodiment, one or more rollers formed to be contacted with the first and second connecting straps may be provided inside the connecting member.

In one exemplary embodiment, the button portion may include an upper portion contacted with an upper surface of the first connecting strap; a lower portion contacted with a lower surface of the first connecting strap; and a middle portion connecting the upper and lower portions to each other, the middle portion moving along the guide groove.

In one exemplary embodiment, the third flexible circuit board may be formed to be electrically connected to the one or more partition straps.

In one exemplary embodiment, the module may include any one or more of a flash module, a camera module, a heart-rate sensor module, a speaker module, a battery module, a display module, a projector module, a Bluetooth headset module, and a smart vehicle key module.

The watch type terminal according to the present disclosure provides advantages as follows.

Modules having various functions are selectively attached/detached to/from the strap, so that a user can easily implement a desired function.

Also, modules can be easily attached/detached to/from the strap by pressurizing attaching/detaching pins.

In addition, a plurality of connecting frames are coupled by hinges, so that each fixing frame and each partition strap can be rotated within a predetermined range.

Further, contact terminals are waterproof-coated, or an O-ring is formed around a charging terminal to be waterproofed.

Further scope of applicability of the present application will become more apparent from the detailed description given hereinafter. However, it should be understood that the detailed description and specific examples, while indicating preferred embodiments of the disclosure, are given by way of illustration only, since various changes and modifications within the spirit and scope of the disclosure will become apparent to those skilled in the art from the detailed description.

BRIEF DESCRIPTION OF THE DRAWING

The accompanying drawings, which are included to provide a further understanding of the disclosure and are incorporated in and constitute a part of this specification, illustrate exemplary embodiments and together with the description serve to explain the principles of the disclosure.

In the drawings.

DETAILED DESCRIPTION OF EXEMPLARY EMBODIMENTS

Figure 1:
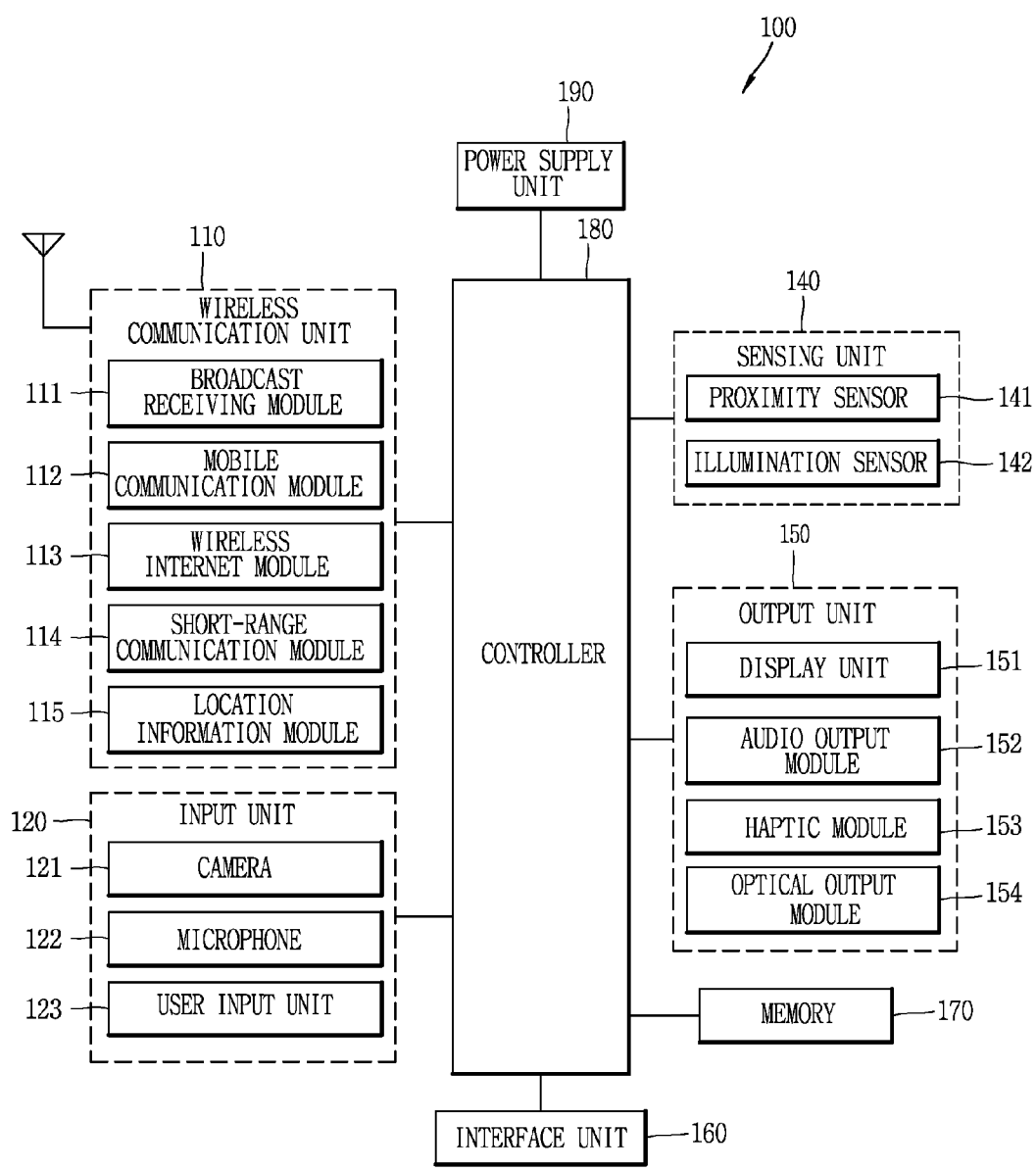
FIG. 1 is a block diagram showing a watch type terminal according to an exemplary embodiment.

Description will now be given in detail according to exemplary embodiments disclosed herein, with reference to the accompanying drawings. For the sake of brief description with reference to the drawings, the same or equivalent components may be provided with the same or similar reference numbers, and description thereof will not be repeated. In general, a suffix such as "module" and "unit" may be used to refer to elements or components. Use of such a suffix herein is merely intended to facilitate description of the specification, and the suffix itself is not intended to give any special meaning or function. In the present disclosure, that which is well-known to one of ordinary skill in the relevant art has generally been omitted for the sake of brevity. The accompanying drawings are used to help easily understand various technical features and it should be understood that the embodiments presented herein are not limited by the accompanying drawings. As such, the present disclosure should be construed to extend to any alterations, equivalents and substitutes in addition to those which are particularly set out in the accompanying drawings.

It will be understood that although the terms first, second, etc. may be used herein to describe various elements, these elements should not be limited by these terms. These terms are generally only used to distinguish one element from another.

It will be understood that when an element is referred to as being "connected with" another element, the element can be connected with the other element or intervening elements may also be present. In contrast, when an element is referred to as being "directly connected with" another element, there are no intervening elements present.

A singular representation may include a plural representation unless it represents a definitely different meaning from the context. Terms such as "include" or "has" are used herein and should be understood that they are intended to indicate an existence of several components, functions or steps, disclosed in the specification, and it is also understood that greater or fewer components, functions, or steps may likewise be utilized.

Mobile terminals presented herein may be implemented using a variety of different types of terminals. Examples of such terminals include cellular phones, smart phones, user equipment, laptop computers, digital broadcast terminals, personal digital assistants (PDAs), portable multimedia players (PMPs), navigators, portable computers (PCs), slate PCs, tablet PCs, ultra books, wearable devices (for example, smart watches, smart glasses, head mounted displays (HMDs)), and the like.

By way of non-limiting example only, further description will be made with reference to particular types of mobile terminals. However, such teachings apply equally to other types of terminals, such as those types noted above. In addition, these teachings may also be applied to stationary terminals such as digital TV, desktop computers, and the like.

FIG. 1 is a block diagram of a mobile terminal in accordance with the present disclosure.

The mobile terminal 100 is shown having components such as a wireless communication unit 110, an input unit 120, a sensing unit 140, an output unit 150, an interface unit 160, a memory 170, a controller 180, and a power supply unit 190. It is understood that implementing all of the illustrated components is not a requirement, and that greater or fewer components may alternatively be implemented.

Referring now to FIG. 1, the mobile terminal 100 is shown having wireless communication unit 110 configured with several commonly implemented components. For instance, the wireless communication unit 110 typically includes one or more components which permit wireless communication between the mobile terminal 100 and a wireless communication system or network within which the mobile terminal is located.

The wireless communication unit 110 typically includes one or more modules which permit communications such as wireless communications between the mobile terminal 100 and a wireless communication system, communications between the mobile terminal 100 and another mobile terminal, communications between the mobile terminal 100 and an external server. Further, the wireless communication unit 110 typically includes one or more modules which connect the mobile terminal 100 to one or more networks. To facilitate such communications, the wireless communication unit 110 includes one or more of a broadcast receiving module 111, a mobile communication module 112, a wireless Internet module 113, a short-range communication module 114, and a location information module 115.

The input unit 120 includes a camera 121 for obtaining images or video, a microphone 122, which is one type of audio input device for inputting an audio signal, and a user input unit 123 (for example, a touch key, a push key, a mechanical key, a soft key, and the like) for allowing a user to input information. Data (for example, audio, video, image, and the like) is obtained by the input unit 120 and may be analyzed and processed by controller 180 according to device parameters, user commands, and combinations thereof.

The sensing unit 140 is typically implemented using one or more sensors configured to sense internal information of the mobile terminal, the surrounding environment of the mobile terminal, user information, and the like. For example, in FIG. 1, the sensing unit 140 is shown having a proximity sensor 141 and an illumination sensor 142.

If desired, the sensing unit 140 may alternatively or additionally include other types of sensors or devices, such as a touch sensor, an acceleration sensor, a magnetic sensor, a G-sensor, a gyroscope sensor, a motion sensor, an RGB sensor, an infrared (IR) sensor, a finger scan sensor, a ultrasonic sensor, an optical sensor (for example, camera 121), a microphone 122, a battery gauge, an environment sensor (for example, a barometer, a hygrometer, a thermometer, a radiation detection sensor, a thermal sensor, and a gas sensor, among others), and a chemical sensor (for example, an electronic nose, a health care sensor, a biometric sensor, and the like), to name a few. The mobile terminal 100 may be configured to utilize information obtained from sensing unit 140, and in particular, information obtained from one or more sensors of the sensing unit 140, and combinations thereof.

The output unit 150 is typically configured to output various types of information, such as audio, video, tactile output, and the like. The output unit 150 is shown having a display unit 151, an audio output module 152, a haptic module 153, and an optical output module 154.

The display unit 151 may have an inter-layered structure or an integrated structure with a touch sensor in order to facilitate a touch screen. The touch screen may provide an output interface between the mobile terminal 100 and a user, as well as function as the user input unit 123 which provides an input interface between the mobile terminal 100 and the user.

The interface unit 160 serves as an interface with various types of external devices that can be coupled to the mobile terminal 100. The interface unit 160, for example, may include any of wired or wireless ports, external power supply ports, wired or wireless data ports, memory card ports, ports for connecting a device having an identification module, audio input/output (I/O) ports, video I/O ports, earphone ports, and the like. In some cases, the mobile terminal 100 may perform assorted control functions associated with a connected external device, in response to the external device being connected to the interface unit 160.

The memory 170 is typically implemented to store data to support various functions or features of the mobile terminal 100. For instance, the memory 170 may be configured to store application programs executed in the mobile terminal 100, data or instructions for operations of the mobile terminal 100, and the like. Some of these application programs may be downloaded from an external server via wireless communication. Other application programs may be installed within the mobile terminal 100 at time of manufacturing or shipping, which is typically the case for basic functions of the mobile terminal 100 (for example, receiving a call, placing a call, receiving a message, sending a message, and the like). It is common for application programs to be stored in the memory 170, installed in the mobile terminal 100, and executed by the controller 180 to perform an operation (or function) for the mobile terminal 100.

The controller 180 typically functions to control overall operation of the mobile terminal 100, in addition to the operations associated with the application programs. The controller 180 may provide or process information or functions appropriate for a user by processing signals, data, information and the like, which are input or output by the various components depicted in FIG. 1, or activating application programs stored in the memory 170. As one example, the controller 180 controls some or all of the components illustrated in FIGS. 1 to 3 according to the execution of an application program that have been stored in the memory 170.

The power supply unit 190 can be configured to receive external power or provide internal power in order to supply appropriate power required for operating elements and components included in the mobile terminal 100. The power supply unit 190 may include a battery, and the battery may be configured to be embedded in the terminal body, or configured to be detachable from the terminal body.

At least some of the above components may operate in a cooperating manner, so as to implement an operation or a control method of a glass type terminal according to various embodiments to be explained later. The operation or the control method of the glass type terminal may be implemented on the glass type terminal by driving at least one application program stored in the memory 170.

Figure 2:
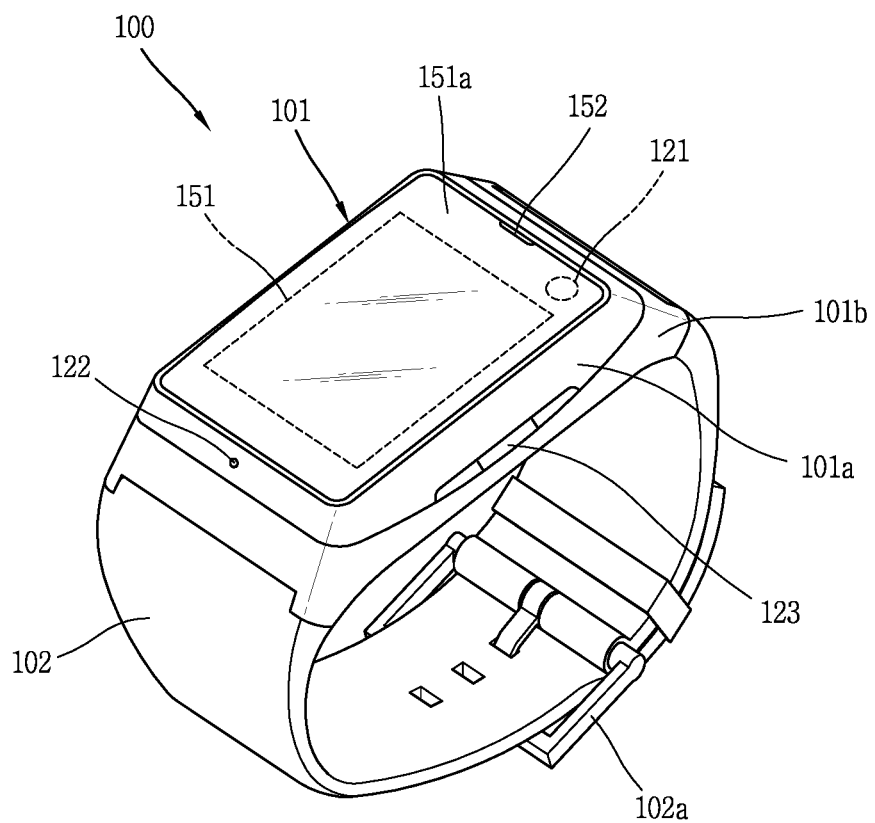
FIG. 2 is a perspective view showing an example of a general watch type terminal according to an exemplary embodiment.

FIG. 2 is a perspective view illustrating one example of a watch-type mobile terminal 100 in accordance with another exemplary embodiment. As illustrated in FIG. 2, the watch-type mobile terminal 100 includes a main body 101 with a display unit 151 and a band 102 connected to the main body 101 to be wearable on a wrist. In general, mobile terminal 100 may be configured to include features that are the same or similar to that of mobile terminal 100 of FIG. 1.

The main body 101 may include a case having a certain appearance. As illustrated, the case may include a first case 101*a* and a second case 101*b* cooperatively defining an inner space for accommodating various electronic components. Other configurations are possible. For instance, a single case may alternatively be implemented, with such a case being configured to define the inner space, thereby implementing a mobile terminal 100 with a uni-body.

The watch-type mobile terminal 100 can perform wireless communication, and an antenna for the wireless communication can be installed in the main body 101. The antenna may extend its function using the case. For example, a case including a conductive material may be electrically connected to the antenna to extend a ground area or a radiation area.

The display unit 151 is shown located at the front side of the main body 101 so that displayed information is viewable to a user. In some embodiments, the display unit 151 includes a touch sensor so that the display unit can function as a touch screen. As illustrated, window 151*a* is positioned on the first case 101*a* to form a front surface of the terminal body together with the first case 101*a*.

The illustrated embodiment includes audio output module 152, a camera 121, a microphone 122, and a user input unit 123 positioned on the main body 101. When the display unit 151 is implemented as a touch screen, additional function keys may be minimized or eliminated. For example, when the touch screen is implemented, the user input unit 123 may be omitted.

The band 102 is commonly worn on the user's wrist and may be made of a flexible material for facilitating wearing of the device. As one example, the band 102 may be made of fur, rubber, silicon, synthetic resin, or the like. The band 102 may also be configured to be detachable from the main body 101. Accordingly, the band 102 may be replaceable with various types of bands according to a user's preference.

In one configuration, the band 102 may be used for extending the performance of the antenna. For example, the band may include therein a ground extending portion (not shown) electrically connected to the antenna to extend a ground area.

The band 102 may include fastener 102*a*. The fastener 102*a* may be implemented into a buckle type, a snap-fit hook structure, a Velcro® type, or the like, and include a flexible section or material. The drawing illustrates an example that the fastener 102*a* is implemented using a buckle.

Figure 3:
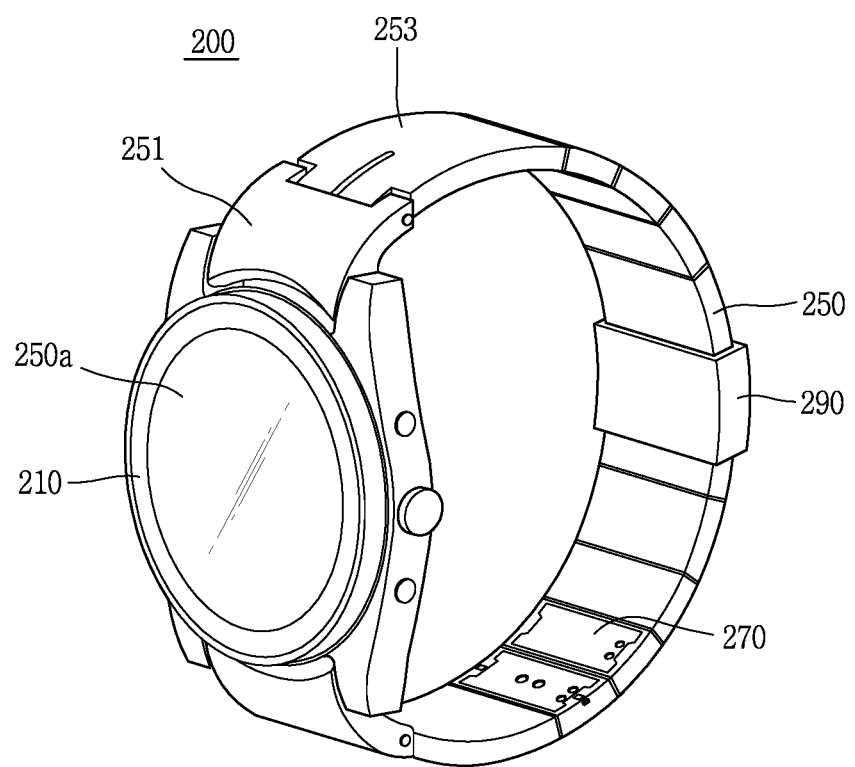
FIG. 3 is a perspective view showing a watch type terminal viewed from the front according to an exemplary embodiment.
Figure 4:
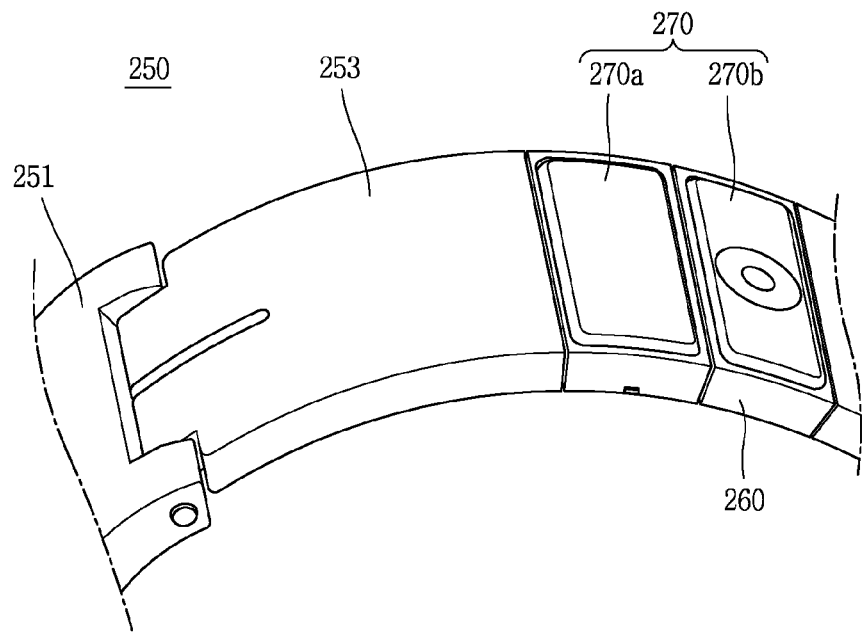
FIG. 4 is a partial perspective view of a strap of the watch type terminal in a state in which a module is attached to the strap according to the exemplary embodiment.
Figure 5:
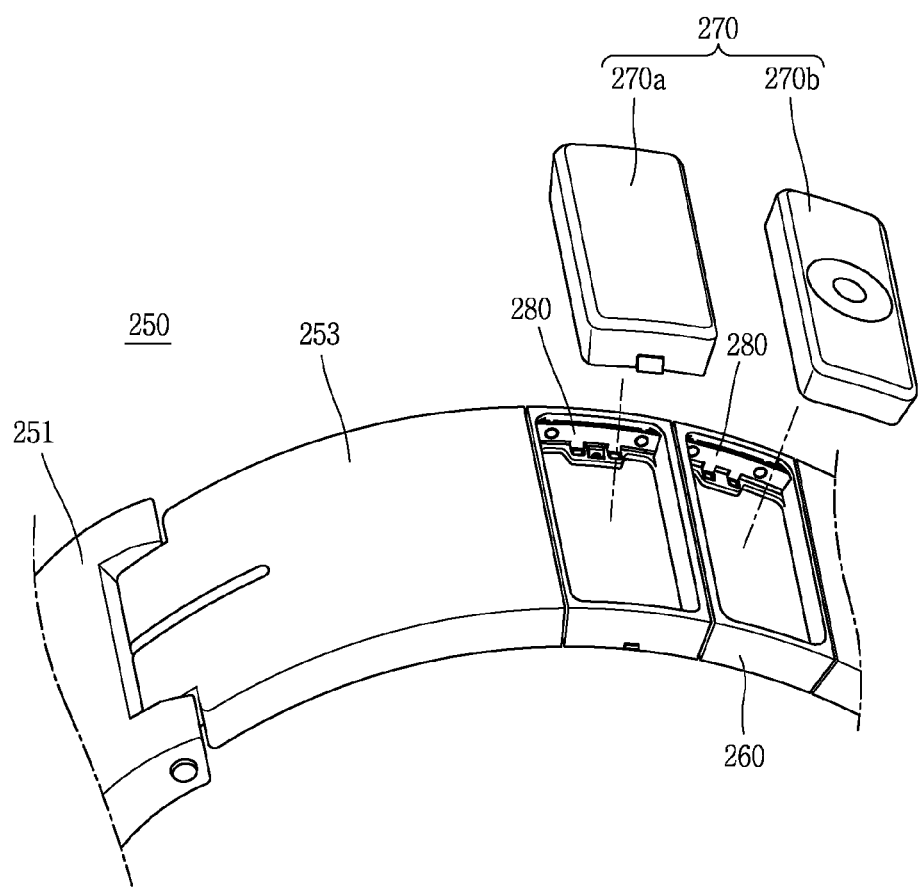
FIG. 5 is a partial perspective view of the strap before the module is attached to the strap in FIG. 4.

FIG. 3 is a perspective view showing a watch type terminal viewed from the front according to an exemplary embodiment. FIG. 4 is a partial perspective view of a strap of the watch type terminal in a state in which a module is attached to the strap according to the exemplary embodiment. FIG. 5 is a partial perspective view of the strap before the module is attached to the strap in FIG. 4.

The watch type terminal 200 according to the exemplary embodiment includes a main body 210 and a strap 250 connected to the main body 210, and the strap 250 is composed of a plurality of pieces.

One or more modules 270 are received in a portion of the strap 250. That is, in the watch type terminal 200, the space in which various components are to be mounted is insufficient due to a limitation of size of the watch type terminal 200, and therefore, the performance of the watch type terminal 200 is limited as compared with mobile terminals such as a tablet. In order to overcome this limitation, in the exemplary embodiment, the module 270 having a specific function is coupled to the strap 250, so that the function of the module 270 can also be implemented in the watch type terminal 200. For example, if a camera module 270*b* is fastened to the watch type terminal 200 having no camera, pictures can be photographed when a user desires to do so. That is, when the user desires to implement a function which is originally provided to the watch type terminal 200 or to be complemented even though the function is originally provided to the watch type terminal 200, the module having the function is fastened to the strap 250, thereby improving user's convenience.

Figure 13:
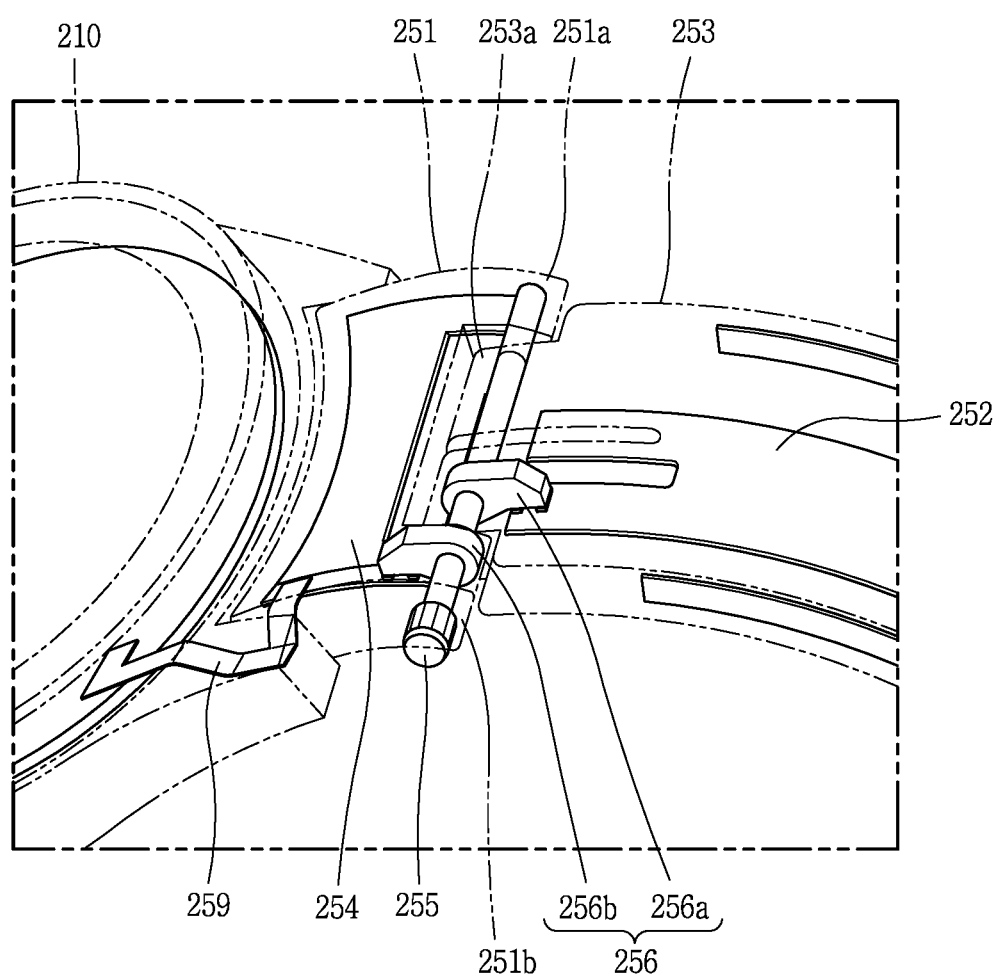
FIG. 13 is a partial transparent view of the watch type terminal according to the exemplary embodiment.

FIG. 13 is a partial transparent view of the watch type terminal according to the exemplary embodiment. Referring to FIG. 13 together with FIGS. 3 to 5, the strap 250 includes partition straps 260 receiving one or more modules 270 therein. In addition, the watch type terminal 200 according to the exemplary embodiment may further include a first strap 251 connected to the main body 210, the first strap 251 being provided with a first flexible circuit board 254 electrically connected to a main circuit board (not shown) provided to the main body 210, and a second strap 253 separably fastened to the first strap 251, the second strap 253 being provided with a second flexible circuit board 252 electrically connected to the first flexible circuit board 254.

In this case, the first strap 251 or the second strap 253 may be omitted. If the second strap 253 is omitted, the first strap 251 may be immediately connected to the partition strap 260. If the first strap 251 is omitted, the second strap 253 may be immediately connected to the main body 210. That is, both the first strap 251 and the second strap 253 are not necessarily provided, and it is sufficient as long as a structure capable of connecting the partition strap 260 and the main body 210 to each other is provided.

In this instance, a third flexible circuit board 280 provided to the partition strap 260 is to be electrically connected to the main circuit board provided to the main body 210. Hereinafter, for convenience, a case where both the first strap 251 and the second strap 253 are provided will be described. However, the present disclosure is not necessarily limited thereto, and as described above, it is sufficient as long as a structure capable of connecting the partition strap 260 and the main body 210 to each other is provided.

The partition strap 260 is provided with the third flexible circuit board 280 which is electrically connected to the second flexible circuit board 252 provided to the second strap 253, to be electrically connected to the main circuit board. The partition strap 260 is connected to another partition strap 260 formed adjacent thereto, and a plurality of partition straps 260 formed adjacent to each other have a structure capable of being bent according to a user's wrist.

As shown in FIGS. 4 and 5, if the module 270 is provided to the strap 250, the module 270 and the strap 250 are integrally formed, thereby forming one strap 250. In this instance, the one or more partition straps 260 and the second strap 253 are connected to each other by a pair of internal frames 220 (see FIG. 8) respectively formed at both sides thereof. When the partition strap 260 is provided in plurality, the internal frames 220 connect the partition straps 260 to each other.

Figure 6:
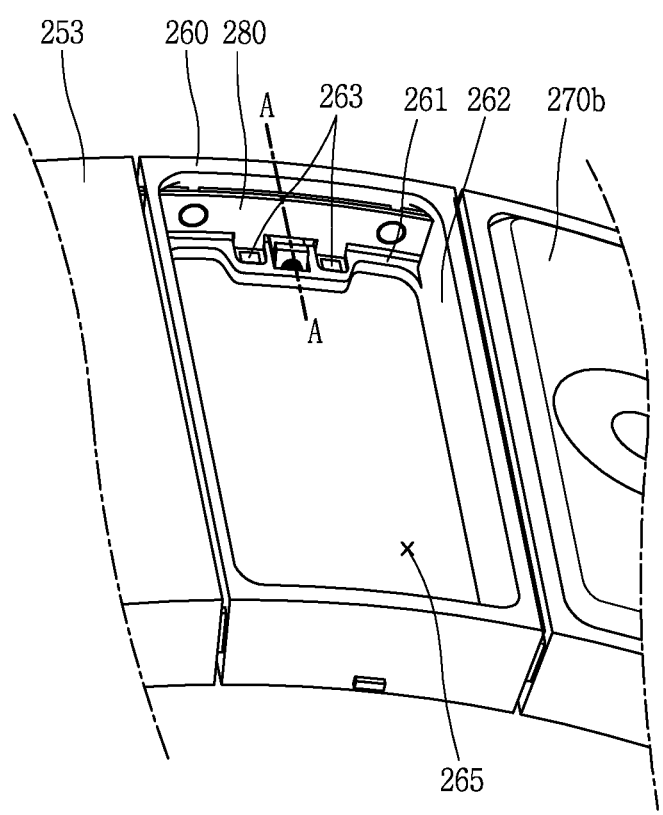
FIG. 6 is an internal perspective view of a partition strap according to the exemplary embodiment.

FIG. 6 is an internal perspective view of the partition strap 260 according to the exemplary embodiment. Referring to FIG. 6, the partition strap 260 includes a wall portion 262 to which the internal frames 220 and the third flexible circuit board 280 are provided, and a bottom portion 261 formed vertically from the wall portion 262, the bottom portion 261 having a through-hole 265 formed therein to support the module 270. That is, the space of the partition strap 260 is mostly empty, and it is sufficient as long as the partition strap is provided with only a portion for receiving the module 270 and a portion electrically connected to the module 270.

Figure 7:
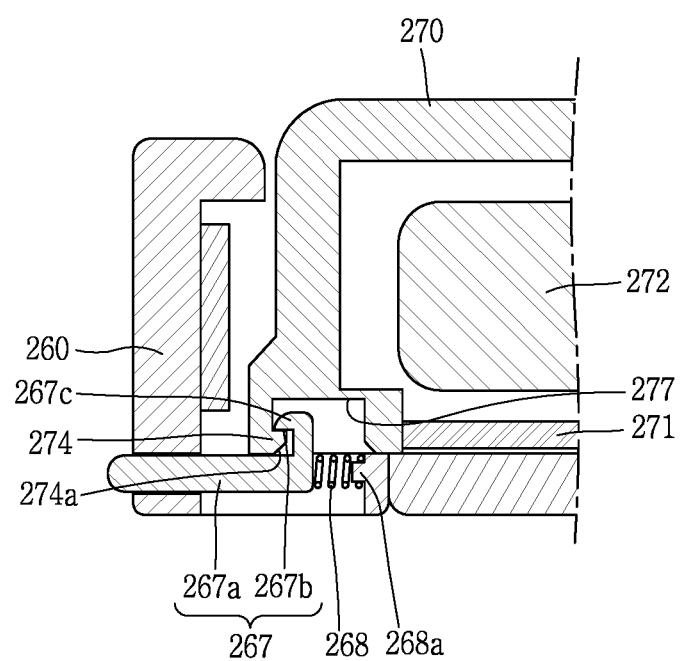
FIG. 7 is a sectional view taken along line AA of FIG. 6.

FIG. 7 is a sectional view taken along line AA of FIG. 6. Referring to FIG. 7, the watch type terminal 200 according to the exemplary embodiment further includes an attaching/detaching pin 267 formed at least one side of the partition strap 260 to selectively fasten the module 270 to the partition strap 260, the attaching/detaching pin 267 being formed toward the inside the partition strap 260 by penetrating the partition strap 260, and an elastic member 268 provided at a position opposite to the attaching/detaching pin 267 to attach/detach the module 270 to/from the partition strap 260.

The attaching/detaching pin 267 includes a body 267a formed by penetrating a lower portion of the partition strap 260, and a first hook 267b formed at one end portion of the attaching/detaching pin 267. A second hook 274 latched to the first hook 267b is formed at a bottom surface of the module 270 such that the attaching/detaching pin 267 is selectively fastened to the module 270 by the elastic member 268. The second hook 274 is formed in a groove 277 provided in the bottom surface of the module 270.

In this instance, the elastic member 268, as shown in FIG. 6, is formed at a portion at which the wall portion 262 and the bottom portion 261 intersect each other. The elastic member 268 is fixed to a projection 268a formed at one point of the bottom portion 261 so as not to be separated. The elastic member 268 may be, for example, a coil spring or a torsion spring.

As shown in FIG. 7, portions 267c and 274a respectively adjacent to the latched portions of the first and second hooks 267b and 274 are formed to be inclined. Thus, when the module 270 moves toward the attaching/detaching pin 267, the inclined portions 267c and 274a are naturally inserted while being slidingly contacted with each other. If the module 270 is inserted into the space of the partition strap 260 once, the first and second hooks 267b and 274 are latched to each other by the elastic force of the elastic member 268, so that the module 270 is not separated from the partition strap 260.

Meanwhile, if the attaching/detaching pin 267 is pushed inward so as to separate the module 270 from the partition strap 260, the latching between the first and second hooks 267b and 274 is released, the module 270 is removed in the state in which the latching between the first and second hooks 267b and 274 is released, so that the module 270 and the partition strap 260 can be separated from each other. In this case, the attaching/detaching pin 267 may be formed at one side or both sides of the partition strap 260.

Figure 8:
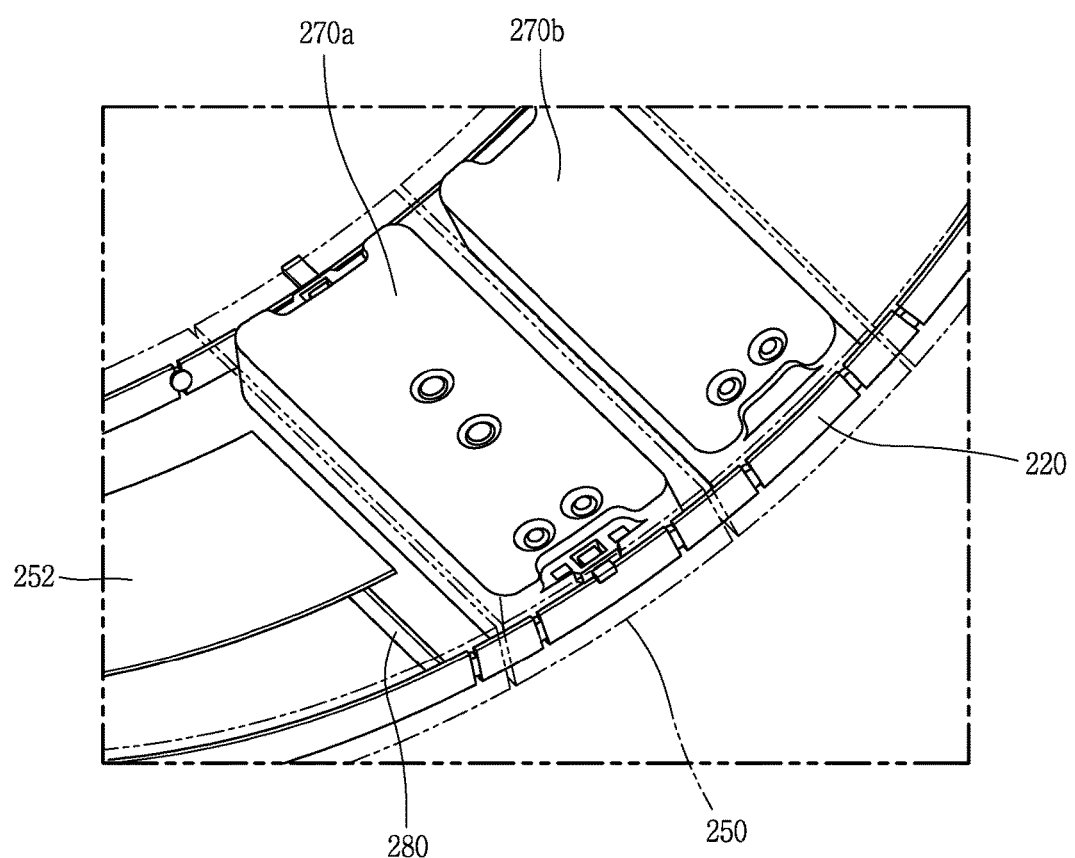
FIG. 8 is a partial transparent view showing a state in which the module is fastened to the strap according to the exemplary embodiment.
Figure 9:
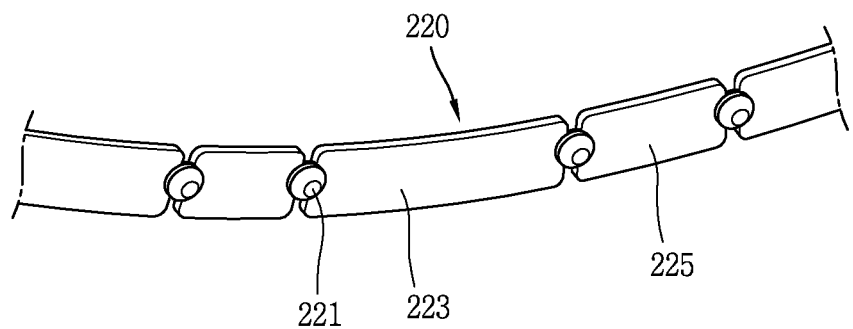
FIG. 9 is a perspective view of an internal frame according to the exemplary embodiment.
Figure 10:
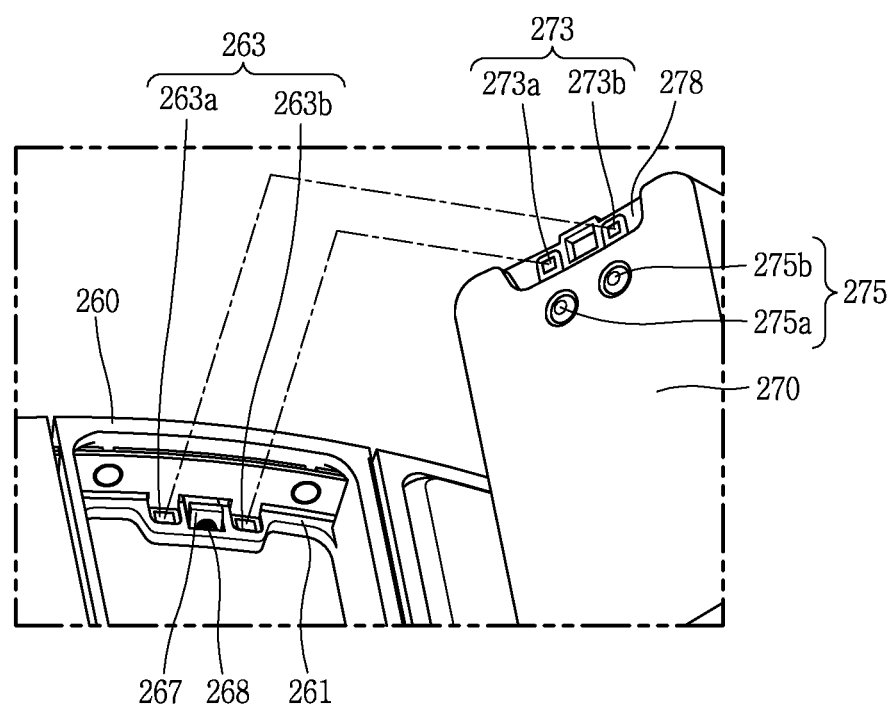
FIG. 10 is a view illustrating that first and second contact terminals are contacted with each other according to the exemplary embodiment.
Figure 11:
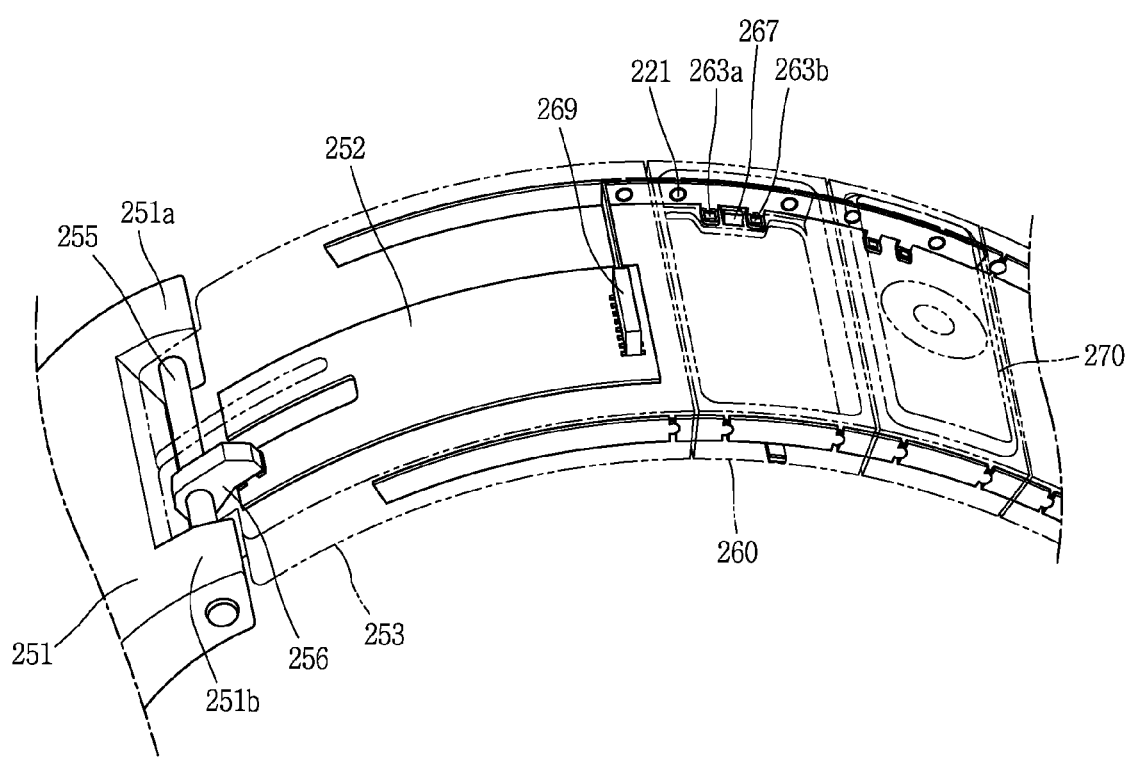
FIG. 11 is a partial transparent view of the strap illustrating that a second flexible circuit board and a third flexible circuit board are connected to each other according to the exemplary embodiment.
Figure 12:
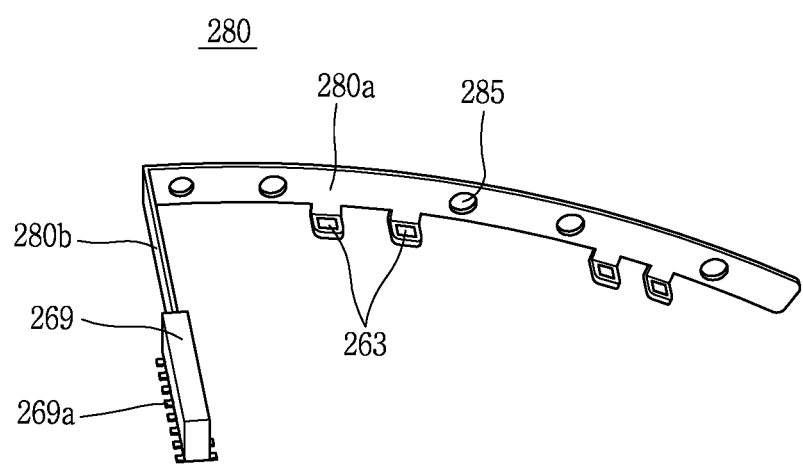
FIG. 12 is a perspective view of the third flexible circuit board according to the exemplary embodiment.

FIG. 8 is a partial transparent view showing a state in which the module is fastened to the strap according to the exemplary embodiment. FIG. 9 is a perspective view of the internal frame 220 according to the exemplary embodiment. FIG. 10 is a view illustrating that first and second contact terminals 263 and 273 are contacted with each other according to the exemplary embodiment. FIG. 11 is a partial transparent view of the strap illustrating that the second flexible circuit board and the third flexible circuit board are connected to each other according to the exemplary embodiment. FIG. 12 is a perspective view of the third flexible circuit board according to the exemplary embodiment.

Hereinafter, the watch type terminal 200 according to the exemplary embodiment will be described in detail with reference to FIGS. 8 to 12.

First, as shown in FIG. 9, the internal frame 220 includes a fixing frame 223 fixed to each partition strap 260, and a connecting frame 225 connected to the fixing frame 223, the connecting frame 225 connecting the adjacent partition straps 260 or the partition strap 260 and the second strap 253 to each other. That is, the fixing frame 223 and the connecting frame 225 are individually formed to rotate independently. However, the fixing frame 223 and the connecting frame 225 are connected by a hinge 221 such that each of the fixing frame 223 and the connecting frame 225 can be rotated about its end portion. As such, the fixing frame 223 and the connecting frame 225 individually rotate, so that the strap 250 to which the internal frame 220 is fixed can be bent to fit a user's wrist.

In this instance, the connecting frame 225 functions to connect the fixing frames 223 to each other, and hence is formed smaller than the fixing frame 223. Each fixing frame 223 is to be fastened to the module 270 to be integrally rotatable with the module 270, and hence the hinge 221 is formed at both ends of the fixing frame 223. Also, the hinge 221 is formed at both ends of the connecting frame 225, to connect the fixing frame 223 and the connecting frame 225 to each other.

According to the structure described above, as the fixing frame 223 or the connecting frame 225 is rotated about its end portion, the fixing frame 223 or the connecting frame 225 can be bent to fit the user's wrist. To this end, both ends of the fixing frame 223 and the connecting frame 225 may be formed to partially overlap each other. Alternatively, a hole (not shown) through which the hinge 221 can pass may be formed both the ends of the fixing frame 223 and the connecting frame 225 such that only portions of the hole overlap each other.

The third flexible circuit board 280 includes a supporting portion 280a provided at the inside of the internal frame 220, the supporting portion 280a having a plurality of through-holes 285 formed therein, and a connecting portion 280b extending from the supporting portion 280a, the connecting portion 280b being connected to the second flexible circuit board 252. The hinge 221, as shown in FIGS. 11 and 12, is inserted into the through-hole 285 formed in the supporting portion 280a to fix the internal frame 220 to the third flexible circuit board 280.

As such, the through-holes 286 into which the hinges 221 of the internal frame 220 are inserted are formed in the supporting portion 280a, and the first contact terminal 263 is bent toward the inside of the terminal 200 from a lower portion of the supporting portion 280a. The third flexible circuit board 280 has an approximately "L" shape, and a connector 269 is connected to an end portion of the connecting portion 280b such that the third flexible circuit board 280 is electrically connected to the second flexible circuit board 252. A plurality of electrodes 269a are provided to the connector 269, and the connector 269 is provided with electrodes 269 required to drive the one or more modules 270. A signal of each module 270 may be transmitted to the main circuit board formed in the main body 210 through the connector 269, or a signal from the main circuit board may be transmitted to the module 270.

FIG. 13 is a partial transparent view illustrating that the main body 210 of the watch type terminal 200 and the strap 250 are connected to each other according to the exemplary embodiment. Referring back to FIGS. 11 and 12 together with FIG. 13, the first flexible circuit board 254 is provided to the first strap 251 directly connected to the main body 210, and the second flexible circuit board 252 is provided to the second strap 253 connected to the first strap 251. The first and second flexible circuit boards 254 and 252 are electrically connected to each other.

To this end, in the exemplary embodiment, a connecting pin 255 connecting the first and second straps 251 and 253 to each other is provided, a fixing member 256 including a pair of fixing members 256a and 256b is provided to the connecting pin 255. The fixing member 256 includes first and second fixing members 256a and 256b. The first fixing member 256a is electrically connected to the second flexible circuit board 252 provided to the second strap 253, and the second fixing member 256b is electrically connected to the first flexible circuit board 254 provided to the first strap 251. The first fixing member 256a may be provided inside the second strap 253, and the second fixing member 256b may be provided inside the first strap 251.

Figure 14:
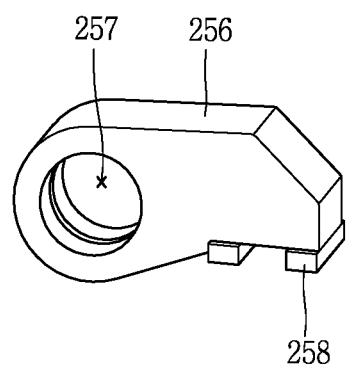
FIG. 14 is a perspective view of a fixing member according to the exemplary embodiment.

FIG. 14 is a perspective view of the fixing member 256 according to the exemplary embodiment. Referring to FIG. 14, a through-hole 257 is formed at one side of the fixing member 256 such that the connecting pin 255 is inserted into the through-hole 257, and a contact terminal 258 is provided at the other side of the fixing member 256 such that the fixing member 256 is electrically connected to the first flexible circuit board 254 or the second flexible circuit board 252. The shape of the fixing member 256 is not particularly limited, and the fixing member 256 may have any shape as long as it has a structure contactable with the flexible circuit board.

In this case, the first flexible circuit board 254 may be connected to the main body 210 by an auxiliary circuit board 259, and the auxiliary circuit board 259 is provided at an end portion of the main body 210. In order to connect the first and second straps 251 and 253 to each other, both ends 251a and 251b of a portion facing the second strap 253 in the first strap 251 are formed to further protrude, and a middle portion 253a of a portion facing the first strap 251 in the second strap 253 is located on the same line to be fastened to the both the ends 251a and 251b of the first strap 251 by the connecting pin 255. Here, the fixing member 256 and the connecting pin 255 may be made of a metal member.

As shown in FIG. 10, in the exemplary embodiment, the first contact terminal 263 extending from a lower portion of the supporting portion 280a to be received at the bottom portion 261 is provided, and the second contact terminal 273 disposed at a lower end of the module 270 to be contacted with the first contact terminal 263 is provided. The first and second contact terminals 263 and 273 are formed with pairs of contact terminals 263a, 263b, 273a, and 273b, respectively. The pair of contact terminals 263a and 263b of the first contact terminal 263 are contacted with the pair of contact terminals 273a and 273b of the second contact terminal 273, respectively. The first and second contact terminals 263 and 273 are waterproof-coated, so that although moisture is introduced into the watch type terminal 200 from the outside, there is no difficulty in operating the watch type terminal 200.

The lower surface of the module 270 is a portion directly contacted with a user's body, and the bottom portion 261 is also a portion directly contacted with the user's body. Hence, a recess portion 278 mounted at the portion where the first contact terminal 263 of the bottom portion 261 in the bottom surface of the module 270 is formed to be further recessed than other portions from the lower surface of the module 270.

Meanwhile, in the exemplary embodiment, the module 270 includes an internal circuit board 271 electrically connected to the third flexible circuit board 280, and a battery 272 for operating the module 270 (see FIG. 7). The internal circuit board 271 corresponds to a controller for controlling the module 270, and the battery 272 supplies power used to operate the module 270 other than the main body 210. The internal circuit board 271 provided in the module 270 is electrically connected to the main circuit board of the main body 210 through the supporting portion 280a of the third flexible circuit board 280. When the module 270 is provided in plurality, the internal circuit boards 271 provided in the plurality of modules 270 are connected to the supporting portion 280a formed long, so that the plurality of modules 270 are electrically connected to the partition strap 260 and the main body 210.

Figure 19:
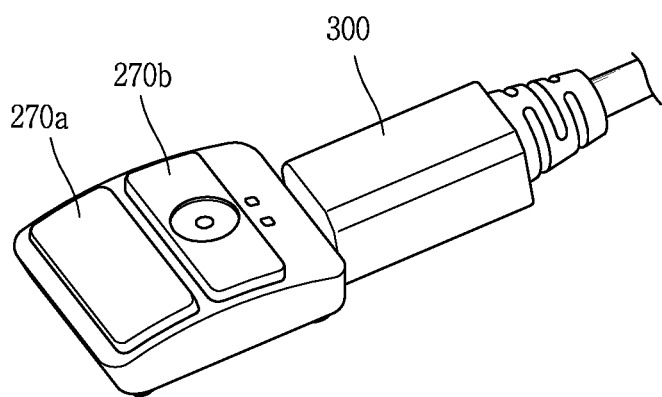
FIG. 19 is a view showing a state in which the module is charged by a charging kit according to the exemplary embodiment.

The battery 272 is provided in each module 270, so that the amount of power used in a main battery (not shown) provided in the main body 210 can be reduced when the module 270 is driven. In the exemplary embodiment, as shown in FIG. 19, the battery 272 of the module 270 may be charged by a charging kit 300. To this end, a charging terminal 275 for charging the battery 272 is provided at the lower surface of the module 270. The charging terminal 275 is formed at the recess portion 278 formed at the lower surface of the module 270, and an o-ring 276 surrounding the charging terminal 275 is provided around the charging terminal 275. The first and second contact terminals 263 and 273 may be plated and waterproof-coated for the purpose of corrosion prevention.

Figure 15A:
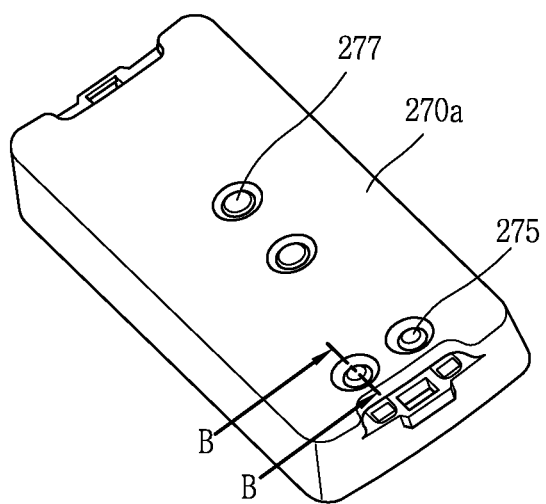
FIG. 15A is a rear perspective view of a heart-rate sensor module according to the exemplary embodiment.
Figure 15B:
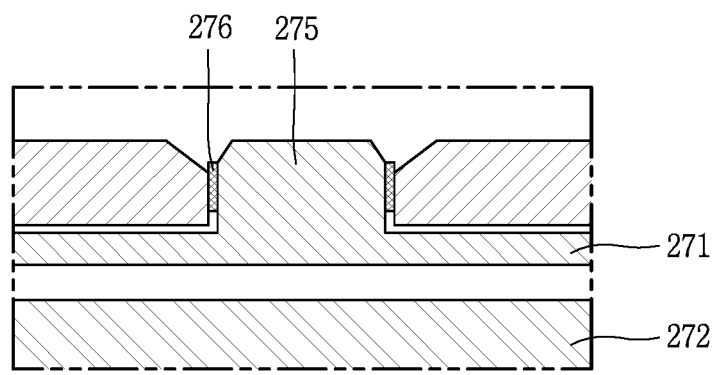
FIG. 15B is a sectional view taken along line BB of FIG. 15A.

FIG. 15A is a rear perspective view of a heart-rate sensor module 270a according to the exemplary embodiment, and FIG. 15B is a sectional view taken along line BB of FIG.

15A. Referring to FIGS. 15A and 15B, in the heart-rate sensor module 270a, a sensing portion 277 directly contacted with a human body is provided at a lower surface of the heart-rate sensor module 270a, and a charging terminal 275 for charging a battery provided inside the heart-rate sensor module 270a is provided at the lower surface of the heart-rate sensor module 270a. The sensing portion 277 and the charging terminal 275 are exposed to the outside. Hence, when water is introduced into the heart-rate sensor module 270a from the outside, a structure for preventing the introduction of water is required. To this end, in the exemplary embodiment, as shown in FIG. 15B, an O-ring 276 is formed at a portion surrounding the charging terminal 275. This is identically applied to the sensing portion 277, and therefore, the O-ring 276 is formed to surround the sensing portion 277.

In the exemplary embodiment, the module 270 may include any one or more of a flash module, a camera module, a heart-rate sensor module, a speaker module, a battery module, a display module, a projector module, a Bluetooth headset module, and a smart vehicle key module. When the module 270 received at the strap 250 is a flash module, light required to photograph pictures may be provided. The flash module may be a flash LED.

When the module is the camera module 270b, the camera module 270b is mounted to the strap 250 even when any camera is not mounted in the watch type terminal 200, so that it is possible to photograph pictures.

When the module 270 is the heart-rate sensor module 270a, a user's heart rate may be measured when the user plays a sport or in an emergency situation. The hear-rate sensor module may be used as an example of sensor modules for health care, but is not limited thereto. For example, the heart-rate sensor module may be a health care module such as a pedometer.

When the module 270 is a speaker module, the speaker module may be used to obtain various sound effects such as a stereophonic sound. The speaker module may be used to simply amplify the magnitude of a sound. The sound output unit 152 is also provided in the watch type terminal 200, but the magnitude of a sound output from the sound output unit 152 is frequently limited. In addition, the sound output unit 152 of the watch type terminal 200 implements only a simple sound effect. Therefore, the speaker module may be used to complement the sound output unit 152.

When the module 270 is a battery module, the battery module assists the main battery provided in the watch type terminal 200 such that the watch type terminal 200 can be used for a longer time. The battery module can be charged by the charging kit 300, and thus the charging of the watch type terminal 200 is further free. That is, if the charging kit 300 for charging the module 270 is provided even though any cable, etc. for charging the watch type terminal 200 does not exist, a battery of the battery module can be charged, so that the degree of freedom of charging is improved.

When the module 270 is a display module, the display module may replace or assist the display unit 250a of the watch type terminal 200. Particularly, when different screens are to be displayed on the display module together with the display unit 250a of the watch type terminal 200, it is possible to implement dual display.

When the module 270 is a projector module, the projector module may not only enlarge and display output images but also implement stereoscopic images, holography, etc.

When the module 270 is a Bluetooth headset module, the Bluetooth head set module may be used as a headset through Bluetooth. However, in this case, the Bluetooth headset module may be used by being detached from the strap 250.

When the module 270 is a smart vehicle key module, a smart vehicle key is always carried in the watch type terminal 200, so that it is less likely that the smart vehicle key will be lost. Also, the smart vehicle key is mounted in the watch type terminal 200, so that it is convenience to carry the smart vehicle key.

Meanwhile, in the exemplary embodiment, the battery 272 is provided in each module 270, and therefore, the module 270 may be independently used. For example, the camera module 270b may be as a substitute of a vehicle black box. Also, the camera module 270b may be used to monitor a pet staying at home. That is, when a user desires to monitor a situation of the pet staying at home, the camera module 270b at home is connected to the watch type terminal 200 through wireless communication such as WiFi, so that the user can identify images photographed by the camera module 270b through the watch type terminal 200.

In the case of a health care module, the module such as a pedometer may be independently used by being separated from the watch type terminal 200.

FIG. 19 illustrates a state in which the module 270 is charged by the charging kit 300 according to the exemplary embodiment. As shown in FIG. 19, the module 270 is individually charged by the charging kit 300.

Figure 16:
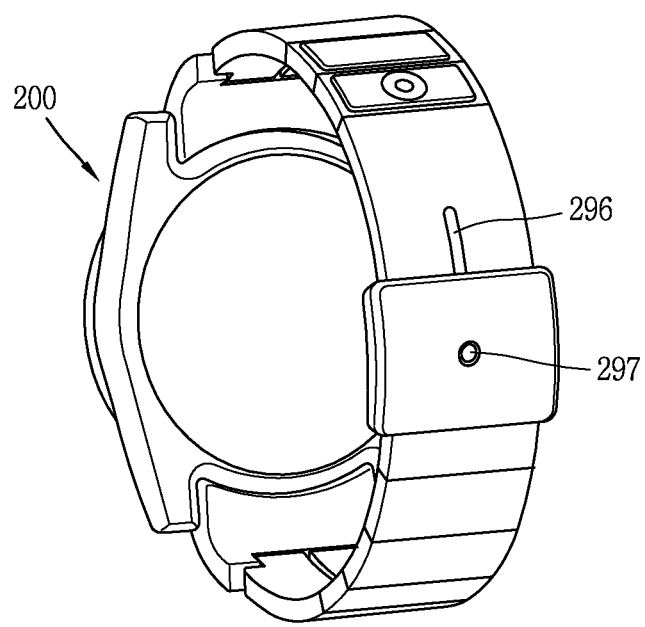
FIG. 16 is a rear perspective view of the watch type terminal according to the exemplary embodiment.
Figure 17:
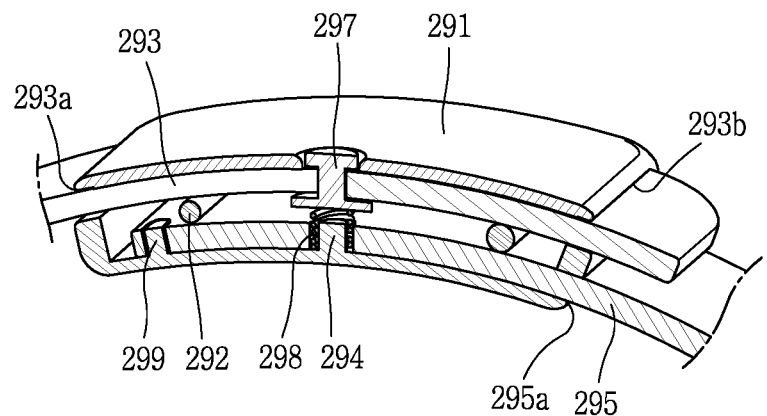
FIG. 17 is a sectional view cut along a guide groove of the strap according to the exemplary embodiment.
Figure 18:
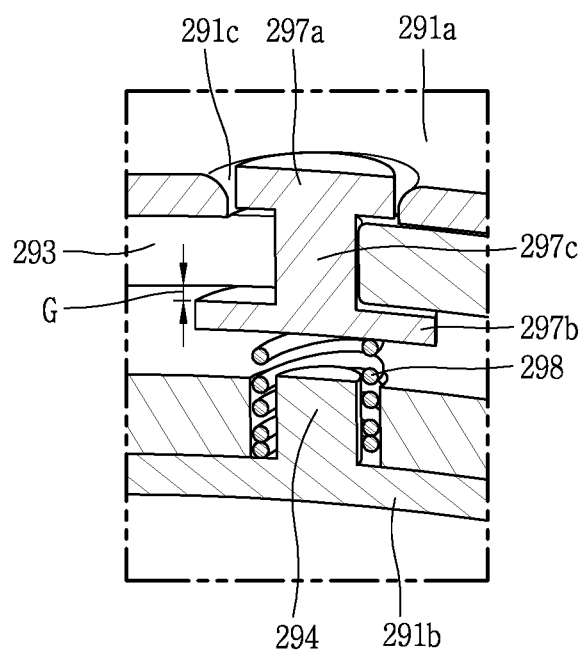
FIG. 18 is a partial enlarged view of FIG. 17.

Meanwhile, FIG. 16 is a rear perspective view of the watch type terminal according to the exemplary embodiment. FIG. 17 is a sectional view cut along a guide groove of the strap according to the exemplary embodiment, which illustrates a connection structure of the strap. FIG. 18 is a partial enlarged view of FIG. 17.

Hereinafter, a connection structure of the strap 250 in the watch type terminal 200 will be described with reference to FIGS. 16 to 18.

Like a general watch, the strap 250 according to the exemplary embodiment is separated at least one portion, to be easily separated from a user.

The watch type terminal 200 according to the exemplary embodiment further includes, at the separated portion, a first connecting strap 293 provided further outward and a second connecting strap 295 provided at the inside of the first connecting strap 293, the second connecting strap 295 having at least one portion disposed to overlap the first connecting strap 293. The size of the overlapping portion of the first and second connecting straps 293 and 295 is adjusted, so that the length of the strap 250 can be changed.

In this case, at least portions of the first and second connecting straps 293 and 295 are inserted into a hollow shape connecting member 291 having an internal space, and through-holes 293a, 293b, and 295a are formed in the forming direction of the strap 250 in the connecting member 291 such that at least portions of the first and second connecting straps 293 and 295 are inserted or extracted. That is, in the connecting member 291, the through-holes 293a, 293b, and 295a are formed in a first direction in which the strap 250 is formed long, and a second direction perpendicular to the first direction is blocked, so that the first and second connecting straps 293 and 295 are inserted or extracted along only the first direction. That is, the through-holes 293a and 293b are formed at positions spaced apart at the same distance toward a lower portion from an upper surface 291a of the connecting member 291 such that the first connecting strap 293 is inserted or extracted. The through-hole 295a is formed below the through-hole 293b such that the second connection strap 295 is inserted or extracted into or from the connecting member 291.

A guide groove 296 is formed by a predetermined length along the first direction in the first connection strap 293, and a button portion 297 moving on the guide groove 296 is provided inside the connecting member 291. An elastic member 298 for providing an elastic force to the button portion 297 is provided under the button portion 297. In this state, the first and second connecting straps 293 and 295 are formed in parallel to each other while maintaining a constant distance, and the connecting member 291 is formed to surround a portion of the portion at which the first and second connecting straps 293 and 295 are formed in parallel to each other. The elastic member 298 may be a torsion spring, and is fixed to a projection 294 formed to protrude from a lower surface 291a.

Referring to FIG. 18, the button portion 297 includes an upper portion 297a contacted with the upper surface 291a of the first connecting strap 293, a lower portion 297b contacted with the lower surface 291b of the first connecting strap 293, and a middle portion 297c connecting the upper and lower portions 297a and 297b to each other, the middle portion 297c moving along the guide groove 296.

Here, the upper surface 291a refers to a portion exposed to the outside when the user wears the watch type terminal 200, and the lower surface 291b refers to a portion directly contacted with the user when the user wears the watch type terminal 200.

As such, the button portion 297 has an approximately "H" shape. The thickness of the middle portion 297c is approximately greater by G than that of the first strap 251. If the lower portion 297b pushes up the first connecting strap 293 toward the upper surface 291a of the connecting member 291 in a state in which the button portion 297 is not pressed, the first connecting strap 293 is not moved. However, if the button portion 297 is pressed, the button portion 297 is moved down while pressing the elastic member 298, and the distance between the upper surface 291a of the connecting member 291 and the lower portion 297b of the button portion 297 becomes greater than the thickness of the first connecting strap 293. Thus, the first connecting strap 293 is in a movable state. That is, the first connecting strap 293 is in a state shown in FIG. 18. In this state, the user moves the first connecting strap 293 while pressing the button portion 297, so that the strap 250 can be adjusted to fit a user's wrist. The upper portion 297a is exposed to the outside through a through-hole 291c formed in the upper surface 291a of the connecting member 291.

In this case, one end portion of the second connecting strap 295 is fixed by a fixing guide 299 formed inside the connecting member 291. The fixing guide 299 is formed in the shape of a projection protruding from the lower surface 291b of the connecting member 291. As the one end portion of the second connecting strap 295 is stuck by the fixing guide 299, the second connecting strap 295 is not moved.

In addition, one or more rollers 292 for allowing the second connecting strap 295 to move smoothly are provided inside the connecting member 291. In FIG. 17, a pair of rollers 292 spaced apart from at a predetermined distance along the first direction are provided inside the connecting member 291. The rollers 292 rotates while being rolling-contacted with a lower surface of the first connecting strap 293 and an upper surface of the second connecting strap 295, thereby allowing the first connecting strap 293 to move smoothly.

Various embodiments may be implemented using a machine-readable medium having instructions stored thereon for execution by a processor to perform various methods presented herein. Examples of possible machine-readable mediums include HDD (Hard Disk Drive), SSD (Solid State Disk), SDD (Silicon Disk Drive), ROM, RAM, CD-ROM, a magnetic tape, a floppy disk, an optical data storage device, the other types of storage mediums presented herein, and combinations thereof. If desired, the machine-readable medium may be realized in the form of a carrier wave (for example, a transmission over the Internet). The processor may include the controller 180 of the mobile terminal.

The foregoing embodiments and advantages are merely exemplary and are not to be construed as limiting the present disclosure. The present teachings can be readily applied to other types of apparatuses. This description is intended to be illustrative, and not to limit the scope of the claims. Many alternatives, modifications, and variations will be apparent to those skilled in the art. The features, structures, methods, and other characteristics of the exemplary embodiments described herein may be combined in various ways to obtain additional and/or alternative exemplary embodiments.

As the present features may be embodied in several forms without departing from the characteristics thereof, it should also be understood that the above-described embodiments are not limited by any of the details of the foregoing description, unless otherwise specified, but rather should be construed broadly within its scope as defined in the appended claims, and therefore all changes and modifications that fall within the metes and bounds of the claims, or equivalents of such metes and bounds are therefore intended to be embraced by the appended claims.

What is claimed is:

1. A watch type terminal, comprising:
a main body; and
a strap coupled to the main body, the strap comprising at least one partition strap shaped to receive a module used for a specific function,
wherein the module is electrically connected to a corresponding one of the at least one partition strap when the module, which is detachable from the at least one partition strap, is coupled to the corresponding one of the at least one partition strap, and
wherein the strap is separated at at least one portion and further comprises, at the separated at least one portion, a first connecting strap provided further outward and a second connecting strap provided at inside of the first connecting strap, the second connecting strap having at least one portion disposed to overlap the first connecting strap;
a connecting member having through-holes formed along a first direction of the first and second connecting straps such that at least portions of the first and second connecting straps are inserted into the connecting member;
a guide groove formed along the first direction in the first connecting strap;
a button portion moving on the guide groove; and
an elastic member provided at a lower portion of the button portion to provide an elastic force to the button portion and remove the first connecting strap from a movable state;
rollers formed on opposite sides of the button to contact the first and second connecting straps.

2. The watch type terminal of claim 1, comprising:
a detachable pin formed extending through a side of the at least one partition strap; and an elastic member contacting the pin and configured to attach or detach the module to or from the at least one partition strap by controlling an elastic force applied to the pin.

3. The watch type terminal of claim 2, wherein:

the pin comprises a first hook formed at an end portion of the pin; and a second hook is formed at a bottom surface of the module, the second hook latched to the first hook when the module is coupled to the at least one partition strap.

4. The watch type terminal of claim 3, wherein the strap further comprises:

a first strap coupled to the main body, the first strap provided with a first flexible circuit board electrically connected to a main circuit board provided to the main body; and a second strap coupled to the first strap, the second strap provided with a second flexible circuit board electrically connected to the first flexible circuit board, wherein the at least one partition strap is provided with a third flexible circuit board electrically connected to the second strap to be electrically connected to the second flexible circuit board, and the at least one partition strap and the second strap are coupled to each other by a pair of internal frames respectively formed at both sides thereof.

5. The watch type terminal of claim 4, wherein the third flexible circuit board comprises:

a supporting portion provided at an inside of the pair of internal frames, the supporting portion having a plurality of through-holes formed therein; and a connecting portion extending from the supporting portion, the connecting portion coupled to the second flexible circuit board.

6. The watch type terminal of claim 5, wherein the internal frame comprises:

a fixing frame fixed to each partition strap; and a connecting frame coupled to the fixing frame, the connecting frame connecting two or more adjacent partition straps to each other or connecting one of the at least one partition strap and the second strap to each other.

7. The watch type terminal of claim 6, wherein:

the fixing frame and the connecting frame are connected by a hinge such that the fixing frame and the connecting frame are individually rotatable; and the hinge is inserted into one of the plurality of through-holes formed in the supporting portion to fix the internal frame to the third flexible circuit board.

8. The watch type terminal of claim 5, wherein the at least one partition strap comprises:

a wall portion to which the internal frame and the third flexible circuit board are provided; and a bottom portion formed vertically from the wall portion, the bottom portion having a through-hole formed therein to support the module.

9. The watch type terminal of claim 8, wherein the third flexible circuit board includes:

a first contact terminal extending from a lower portion of the supporting portion to be received at the bottom portion; and a second contact terminal disposed at a lower end of the module to contact the first contact terminal such that the module and the at least one partition strap are electrically connected to each other.

10. The watch type terminal of claim 9, wherein the first contact terminal and the second contact terminal are waterproof-coated.

11. The watch type terminal of claim 4, wherein the module comprises:

an internal circuit board electrically connected to the third flexible circuit board; and a battery for operating the module.

12. The watch type terminal of claim 11, further comprising a charging terminal for charging the battery, the charging terminal provided at a lower surface of the module.

13. The watch type terminal of claim 12, wherein:

the charging terminal is formed to be exposed to one surface of the module; and an O-ring surrounding the charging terminal is provided around the charging terminal.

14. The watch type terminal of claim 1, wherein a size of the overlapping portion of the first and second connecting straps is adjustable such that a length of the strap is changeable.

15. The watch type terminal of claim 14, wherein the second connecting strap is fixed by a fixing guide formed inside the connecting member.

16. The watch type terminal of claim 14, wherein the button portion comprises:

an upper portion contacting an upper surface of the first connecting strap;

a lower portion contacting a lower surface of the first connecting strap; and a middle portion connecting the upper portion and the lower portion to each other, the middle portion moving along the guide groove.

17. The watch type terminal of claim 4, wherein the third flexible circuit board is formed to be electrically connected to the at least one partition strap.

18. The watch type terminal of claim 1, wherein the module comprises at least one of a flash module, a camera module, a heart-rate sensor module, a speaker module, a battery module, a display module, a projector module, a BLUETOOTH headset module, or a smart vehicle key module.

* * * * *